United States Patent [19]

Houston

[11] 4,129,783
[45] Dec. 12, 1978

[54] HIGH SPEED COMPUTERIZED TOMOGRAPHY IMAGING SYSTEM

[75] Inventor: John M. Houston, Schenectady, N.Y.

[73] Assignee: General Electric Company, Schenectady, N.Y.

[21] Appl. No.: 838,458

[22] Filed: Oct. 3, 1977

Related U.S. Application Data

[63] Continuation-in-part of Ser. No. 683,884, May 6, 1976, abandoned.

[51] Int. Cl.² .................. A61B 6/02; G01N 23/08
[52] U.S. Cl. .................. 250/445 T; 250/360; 250/407
[58] Field of Search .................. 250/445 T, 360, 401, 250/407

[56] References Cited

U.S. PATENT DOCUMENTS

| 4,051,378 | 9/1977 | Krippner | 250/445 T |
| 4,057,725 | 11/1977 | Wagner | 250/445 T |

Primary Examiner—Craig E. Church
Assistant Examiner—T. N. Grigsby
Attorney, Agent, or Firm—Lawrence D. Cutter; Joseph T. Cohen; Marvin Snyder

[57] ABSTRACT

A high speed tomographic x-ray imaging system comprises an array of x-ray sources disposed opposite a closely spaced array of x-ray detectors. Small groups of sources in the array are simultaneously pulsed to provide x-ray transmission data along a number of ray paths through a body undergoing examination. X-ray energy from each source in the array is collimated to illuminate only a small sector of the detector array. High speed, unambiguous x-ray transmission information, is thereby produced.

8 Claims, 4 Drawing Figures

HIGH SPEED COMPUTERIZED TOMOGRAPHY IMAGING SYSTEM

This application is a continuation-in-part of applicant's prior copending application, Ser. No. 683,884, filed May 6, 1976 now abandoned.

This invention relates to computerized x-ray tomographic imaging apparatus. More particularly, this invention relates to tomographic imaging systems wherein a plurality of x-ray sources are simultaneously pulsed to produce x-ray absorption data along a number of intersecting ray paths.

BACKGROUND OF THE INVENTION

Computerized x-ray tomography is a system for producing images of internal body organs which are free from the shadows of intervening structures. Prior art tomographic equipment, has generally, comprised an x-ray source disposed opposite one or more x-ray detectors on a movable structure. The source and detectors rotate and/or translate in a plane which passes through the body organs undergoing examination to produce electrical signals which are representative of x-ray transmission data along a plurality of ray paths. The signals are then combined, usually in digital computer equipment, to reconstruct shadow-free images of interal body sections. Tomography equipment of this type is well known as prior art and described, for example, in U.S. Pat. No. 3,778,614 to Hounsfield and U.S. Pat. No. 3,881,110 to Hounsfield et al.

The rate of production of images in a tomography system which incorporates moving sources and detectors is necessarily limited by the time required to accomplish the physical translation or rotation of the mechanism and is, typically, limited to less than one image per second. Such equipment is, therefore, unsuited for viewing moving body organs, for example, a beating heart. Dr. Earl Wood of the Mayo Clinic in a personal communication has recently proposed a tomographic system for imaging moving body organs wherein a plurality of x-ray sources are sequentially pulsed to rapidly produce x-ray transmission data along a number of diverse ray paths.

Methods and circuits for pulsing x-ray tubes are well known in the x-ray arts and are described, for background purposes, for example, in U.S. Pat. Nos. 1,647,478; 3,333,104; and 3,567,940.

The x-ray detectors utilized in prior art x-ray tomography apparatus have generally comprised scintillation crystals or phosphor screens coupled to optical detectors, for example, image orthicon or photomultiplier tubes. Such devices are rather large and must, generally, be utilized with collimation apparatus to achieve fine spatial resolution. Such scintillation detectors and collimation apparatus are, relatively inefficient detectors of x-ray energy. It is, therefore, necessary to expose a patient undergoing tomographic examination in such equipment to a relatively high dose of ionizing radiation.

My copending patent application Ser. No. 616,930, filed Sept. 26, 1975 and now U.S. Pat. No. 4,031,396 with Nathan R. Whetten describes a high pressure, xenon filled ionization chamber array which is characterized by high detection efficiency and fine spatial resolution when utilized in x-ray tomography equipment. The detector comprises a large plurality of detector cells separated by substantially parallel metal collector plates which may be focused on a single source of diverging x-rays. X-ray photons entering the detector cells produce ion-electron pairs which drift under the influence of an electric field, to the collector plates. Detectors of this type are well suited for the efficient detection of diverging x-ray energy which, for example, may be produced from a single x-ray source and collimated to provide a planar, fan-like spatial distribution. The ion chamber array of that disclosure is, however, relatively inefficient for detecting x-ray energy which originates from an array of spatially separated x-ray sources of the type utilized in the above-described, high speed tomographic equipment. U.S. Pat. Nos. 1,647,48; 3,333,104; 3,567,940; 3,778,614; and 3,881,110 are incorporated herein by reference solely as background material exemplifying prior art.

SUMMARY OF THE INVENTION

In accordance with the present invention, a high speed x-ray tomography apparatus comprises an array of spatially separated, collimated x-ray sources disposed opposite an array of closely spaced x-ray detectors. Each of the x-ray sources is collimated to produce a relatively thin, planar sectorial swath of x-ray photons. X-ray sources in subsets of the array are pulsed simultaneously to obtain x-ray transmission data for tomographic image reconstruction. The collimation and grouping of the x-ray sources as well as the sequence of firing is chosen so that each source in a subset illuminates a separate and distinct sector of the x-ray detector array. The time required to produce a tomographic image is thereby reduced.

An ionization chamber array suitable for use in this tomographic equipment comprises a comb-like array of collector electrodes of a first polarity disposed equi-distant between two parallel sheet electrodes of the opposite polarity and immersed in a high pressure, ionizable gas. X-ray energy enters the detector in a direction substantially parallel to the comb-like electrodes and interacts with the detector gas to produce electron-ion pairs. The electrons and ions drift under the influence of an electric field, in a direction substantially perpendicular to both the direction of the incident x-ray beam and the linear array direction, to the collection electrodes. The detector cells of the present array are not focused on a single x-ray source, as were the cells of the array described in the above-referenced patent disclosure, and are therefore well suited for use in tomography systems having multiple, spatially distributed, x-ray sources.

It is, therefore, an object of this invention to provide a high speed tomographic imaging system for producing clear images of moving body organs.

Another object of this invention is to reduce the time required for the production of x-ray tomographic images.

BRIEF DESCRIPTION OF THE DRAWINGS

The novel features believed characteristic of the present invention are set forth in the appended claims. The invention itself, together with further objects and advantages thereof, may be best understood with reference to the following detail description of the preferred embodiment taken in connection with the appended drawings in which:

DESCRIPTION OF THE PREFERRED EMBODIMENT

Figure 1:
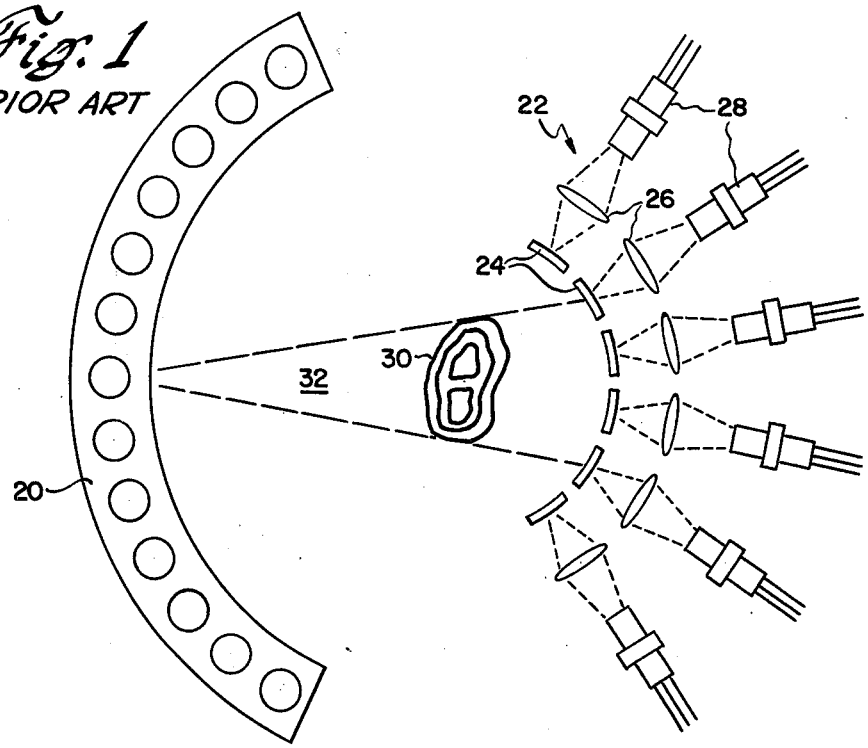
FIG. 1 is a high speed tomography system of the prior art.

FIG. 1 illustrates a high speed x-ray tomography system of the prior art. An array of pulsed x-ray sources 20 is disposed opposite an array of x-ray detectors 22. Each individual x-ray detector of the array 22 comprises a phosphor screen 24 adapted to emit light in proportion to incident x-ray intensity. Light from the screen 24 is focused by a lens 26 on a television camera type pick-up tube, typically an image orthicon 28. Electrical signals, from each tube 28, which represent a linear distribution of x-ray intensities across the width of a screen 24, are transmitted to a digital computer for processing into x-ray tomographic images.

Body structures 30 undergoing examination are interposed between the source array 20 and the detector array 22. Each x-ray source in the array 20 is sequentially pulsed to produce a swath of ionizing radiation 32 which is attenuated in varying degrees by the body structure 30 and impinges on the detector array 22. The individual elements of the array 20 may be pulsed in rapid sequence to provide x-ray transmission information along a plurality of intersecting paths through the body structure 30 from which image information may be constructed. Each source in the array 20, however, necessarily illuminates substantially the entire detector array 22 and the rate of sequential pulsing of the individual sources is, therefore, necessarily limited by the speed at which data may be read from the detector elements (i.e., pick-up tubes 28). Information produced from a single x-ray pulse must be completely read out from a detector 28 before another source in the array 20 is pulsed in order to eliminate a redundancy of information which would occur if x-rays from two sources reached the same tube during a single readout period.

Figure 2:
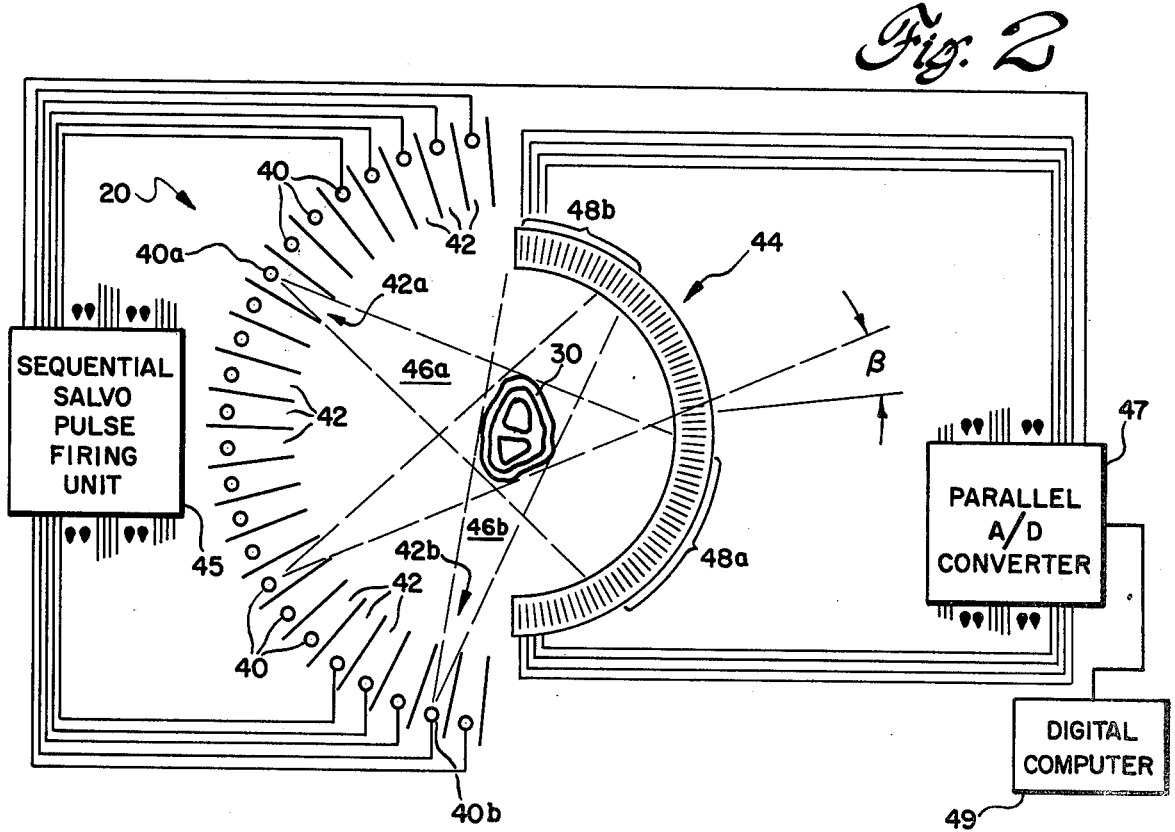
FIG. 2 is a high speed tomography system of the present invention.

FIG. 2 is an improved high speed tomography system of the present invention. A substantially semicircular array of x-ray sources 20 comprises a plurality of individual x-ray tube anodes 40 separated by an array of collimators 42. The geometry of the collimators 42 is selected so that the x-ray beam from each anode 40 is restricted to a substantially planar, sectorial swath. X-ray energy in each swath passes through a body structure 30 and impinges on a curvilinear array of closely spaced, ionization chamber, detectors 44 disposed in the plane of the x-ray swath. The dimensions and geometry of the collimators 42 are adapted to limit the width of each x-ray swath so that it illuminates only a substantially small sector of the array 44. Thus, in the illustration of FIG. 2, x-rays from anode 40a pass through collimator 42a to form a sectorial swath 46a which impinges on a small group 48a of detectors in the array 44. Likewise, x-rays from the anode 40b pass through the collimator 42b and impinge on a separate and distinct group 48b of detectors in the array 44.

The x-ray sources in the array 20 are pulsed in salvos, under the control of the sequential salvo pulse firing control unit 45, the grouping of sources in each salvo being chosen so that the individual sources 40 in the salvo illuminate separate and distinct groups of detectors in the array 44. After each salvo of sources is pulsed, data from the detectors is converted into digital signals by the analog-to-digital converter 47 and is sent to a digital computer 49 for processing and another salvo of sources, similarly chosen to illuminate other distinct detector groups, is pulsed also under control of the firing unit 45. Each detector in the array 44 will, in general, receive x-ray data from a number of sequential salvos. The groups of the individual detectors which are illuminated by the sources in each salvo will, however, change. The number of sources which may be simultaneously pulsed in each salvo is, of course, a function of the system and collimator geometry which, in turn, is determined by the size of the body structure examined, the spatial resolution required, and the desired image production time. Depending on this geometry and the number of detectors and sources in the arrays, the speed of image processing may be increased by a factor of two or more over prior art tomography systems.

Figure 3:
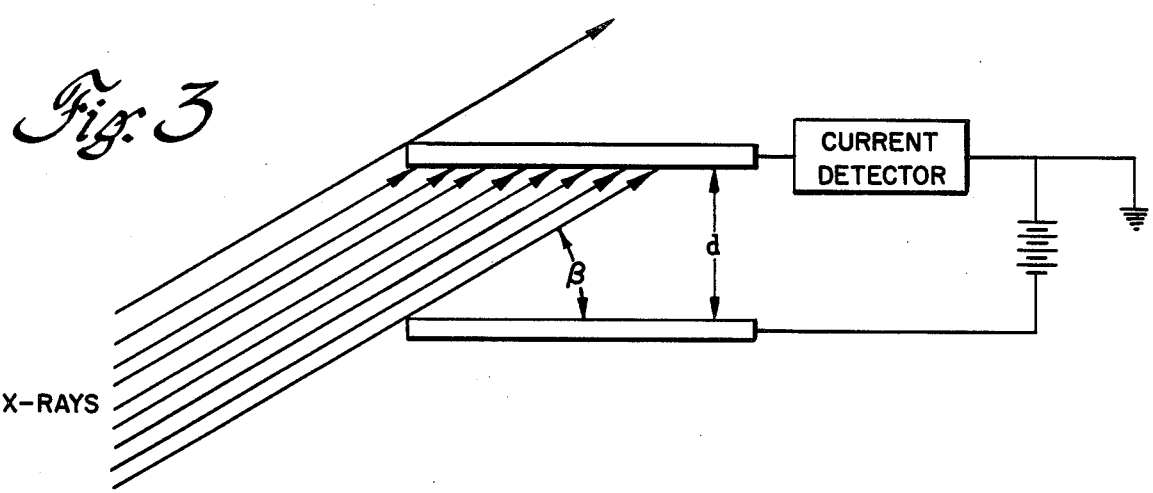
FIG. 3 is a single detector cell of the prior art.

The detector array 44 may comprise ionization chambers of the type described in the above-mentioned United States patent application, Ser. No. 616,930, now issued U.S. Pat. No. 4,031,396, which is incorporated herein, by reference, as background material. That detector comprises an array of detector cells defined between individual sheet collector electrodes which are disposed substantially parallel to the direction of the incident x-ray beam and perpendicular to the plane of the x-ray swath. The individual cells of such a detector are focused on a single source to provide high efficiency x-ray collection and detection, and such a detector is well suited for use in conventional tomography apparatus which comprises a single x-ray source. When used in a multiple source tomography system, this array suffers from a substantial loss of detection efficiency for x-rays which originate off the focal point of its individual cells. The cause of this inefficiency may be noted by reference to FIG. 2 and FIG. 3 which is an enlarged view of an individual detector cell illuminated by the x-rays from a source lying outside its focal region and incident on the plane of the cell at an angle $\beta$. If R is the radius of the detector arc and P is the radius of the field of view at the body 30, the maximum value of the angle $\beta$ occurs at the edge of each view such that $\sin \beta = P/R$. In a typical system of the type illustrated in FIG. 2 used, for example, for viewing a beating heart, P equals approximately 20 centimeters and R equals approximately 75 centimeters, yielding a maximum angle, $\beta$, of 16°. The efficiency of the cell for oblique detection angles is determined by the spacing of the collector electrodes $d$. The spacing $d$ is determined, among other factors, by the degree of spatial resolution required by the system and by the time required for the electrons and ions produced within a cell to drift under the influence of an electric field to the individual electrodes. If, for example, the cell is filled with a xenon detector gas at a pressure of approximately 20 atmospheres, a spacing, $d$, of approximately 1 mm is required to obtain a 1 millisecond response time. The response of such a cell, with 1 millimeter electrode spacing, for x-rays incident at an angle $\beta$ of 16° will be only approximately 14 percent of its efficiency for x-rays incident at an angle of 0°. This loss of efficiency introduces serious calibration problems into image reconstruction algorithms and necessarily increase the radiation dose which is required to produce an image of given resolution. The calibration problem in a multiple source array is, of course, greatly increased by the fact that the angle of incidence of x-rays on each cell is different for each detector and large numbers of calibration factors must, therefore, be stored and utilized.

Figure 4:
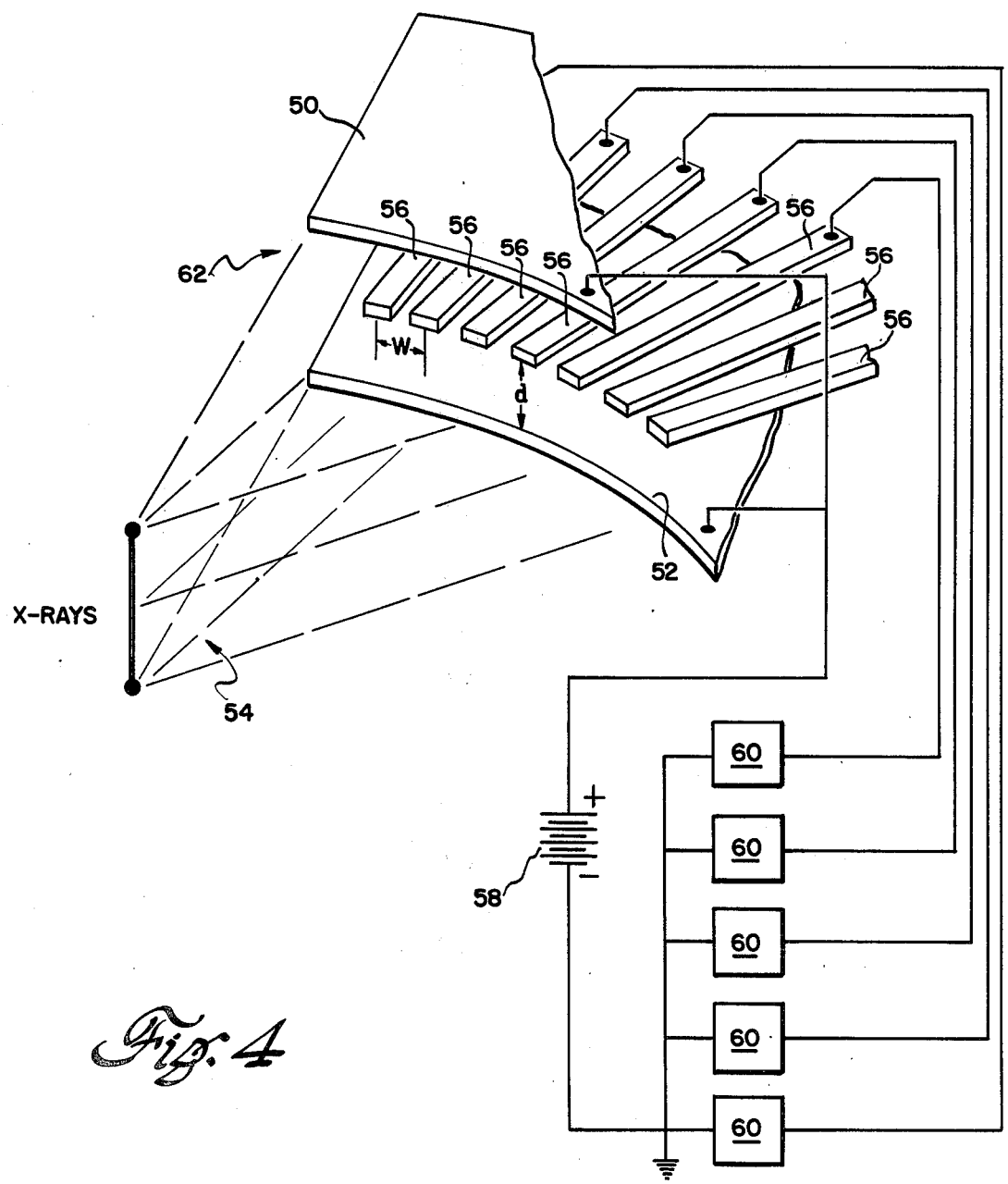
FIG. 4 is an ionization chamber array useful with the present invention.

FIG. 4 is an ion chamber array of the present invention which has a substantially constant detection efficiency for varying angles of x-ray incidence. A pair of planar, conductive anodes 50 and 52 are disposed parallel to an incident sheet of x-ray radiation 54. A plurality of rod-like cathodes 56 are disposed, equi-distant between the anodes 50 and 52 and substantially parallel, one to the other, with their longest dimension generally parallel to the incident x-rays. One terminal of a voltage source 58 is connected to the anode sheets 50 and 52. Each of the cathodes 56 is connected through one of a plurality of current detector circuits 60 to the other terminal of the voltage source 58. In a preferred embodiment of the invention, a common node of the voltage source and the current detectors represents ground potential.

It will be recognized, by those skilled in the art, that the polarity of the voltage source and the position of the ground connection may be varied without affecting the utility of the invention and that the designation of the collection electrodes 50, 52, and 56, as anodes and cathodes is for ease of description only.

A detector gas 62 fills the space between the anode sheets 50 and 52 and the cathodes 56. The gas type, gas pressure, and the spacing W between the electrodes are chosen using methods well known to the art so that a large fraction (typically more than 70 percent) of the incident x-ray photons are absorbed within the gas. The detector gas 62, typically comprises rare gas of high atomic number, for example, xenon, krypton, argon, or a molecular gas comprising atoms having an atomic weight greater than that of argon (i.e., 39.9); at a pressure in the range from approximately 10 atmospheres to approximately 100 atmospheres.

Incident x-rays 54 interact with the detector gas 62 between the anodes 50 and 52 to produce electron-ion pairs. The electrons drift under the influence of the electric field, imposed by the voltage source 58, to the anode plates 50 and 52 while the ions are similarly collected on the cathodes 56. Ion current flow to any individual cathode 56 is proportional to the number of interactions between photons and gas atoms in the region of that cathode so that the distribution of current flow among the individual current detector circuits 60 of the array is a function of the distribution of x-ray intensity along the detector array. The direction of electron an ion motion within the detector is substantially perpendicular to the array length and to the incident x-ray beam.

The cathodes 56 may be arrayed parallel one to the other to produce a linear detector array. Alternately, the detectors may lie at small angles, one to the other, to define a curved or semicircular array of the type illustrated in FIG. 2.

The tomography system of the present invention allows fast and accurate imaging of internal body organs and is insensitive to the blurring effects which motion of those organs tends to produce in prior art systems. The system is also higly efficient for producing moving pictures of body organs, for example, of a beating heart.

While the invention has been described in detail herein in accord with certain preferred embodiments thereof, many modifications and changes therein may be effected by those skilled in the art. Accordingly, it is intended by the following claims to cover all such modifications and changes which fall within the true spirit and scope of the invention.

The invention claimed is:

1. In a high speed, tomographic, x-ray imaging system of the type comprising an array of x-ray sources disposed about a body undergoing examination; an array of x-ray detectors disposed about said body opposite said array of x-ray sources; means for the collection of data produced by said detectors; and means for sequentially pulsing said x-ray sources, the improvement wherein:

said system further comprises collimating means disposed between each of said x-ray sources and said body, said collimating means being adapted to confine the emission of x-ray energy from each x-ray source into an x-ray beam which illuminates only a fraction of the x-ray in said insaid x-ray detector array; and said means for pulsing said x-ray sources are adapted to simultaneously pulse salvos of said x-ray sources, each of said salvos comprising at least two selected x-ray sources in said array, the particular x-ray sources in each of said salvos being selected so that each source in a salvo illuminates a separate and distinct fraction of said x-ray detectors, and said means for detecting said x-ray sources are adapted to be activated in concert with the pulsing of the corresponding x-ray source salvos, and said means for the collection of data are adapted to receive the data produced by said activated detectors.

2. The improved imaging system of claim 1 wherein said array of x-ray sources is a substantially semicircular array.

3. The improved imaging system of claim 2 wherein said array of x-ray detectors is a substantially semicircular array.

4. The improved imaging system of claim 1 wherein said array of x-ray detectors is substantially a semicircular array.

5. The improved imaging system of claim 1 wherein said x-ray detectors are ionization chambers.

6. The improved imaging system of claim 1 wherein said collimating means are further adapted to confine the emission of x-rays emerging from each of said sources into a substantially planar, fan-like beam.

7. A method for generating tomographic image data from body structures comprising the steps of:

disposing an array of x-ray sources about said body structures;

disposing an array of x-ray detectors about said body structures opposite said array of x-ray sources;

collimating x-ray energy from each of said sources into a beam which illuminates only a fraction of said x-ray detector array; and simultaneously pulsing a subset of x-ray sources in said array, the sources in said subset being selected so that x-ray energy from each said simultaneously pulsed sources illuminates a separate and distinct fraction of said x-ray detectors, whereby x-ray transmission data along a plurality of ray paths is obtained in a fast and unambiguous manner.

8. The method of claim 7 comprising the additional step of sequentially pulsing additional subsets of x-ray detectors in said array, the individual detectors in each of said additional subsets being selected so that x-ray energy from each of said detectors in a subset illuminates a separate and distinct fraction of the detectors in said array.